United States Patent
Pozueta Romero et al.

(10) Patent No.: US 7,205,150 B2
(45) Date of Patent: Apr. 17, 2007

(54) TRANSGENIC PLANTS OVER-EXPRESSING PLANT ADP-GLUCOSE PYROPHOSPHATASE

(75) Inventors: Javier Pozueta Romero, Pamplona (ES); Edurne Baroja Fernandez, Pamplona (ES); Aitor Zandueta Criado, Pamplona (ES); Milagros Rodriguez Lopez, Pamplona (ES); Francisco Jose Muñoz Perez, Pamplona (ES)

(73) Assignees: Universidad Publica de Navarra, Pamplona (ES); JCR Pharmaceuticals Co., Ltd., Kasuga-cho, Ashiya (JP)

( * ) Notice: Subject to any disclaimer, the term of this patent is extended or adjusted under 35 U.S.C. 154(b) by 555 days.

(21) Appl. No.: 10/181,993

(22) PCT Filed: Feb. 1, 2001

(86) PCT No.: PCT/ES01/00021

§ 371 (c)(1),
(2), (4) Date: Jan. 24, 2003

(87) PCT Pub. No.: WO01/57196

PCT Pub. Date: Aug. 9, 2001

(65) Prior Publication Data

US 2003/0167536 A1    Sep. 4, 2003

(30) Foreign Application Priority Data

Feb. 2, 2000  (ES) .............................. 200000271
Jul. 28, 2000 (ES) .............................. 200001914

(51) Int. Cl.
| | |
|---|---|
| C12N 15/84 | (2006.01) |
| C12N 5/04 | (2006.01) |
| C12N 15/82 | (2006.01) |
| C12N 15/52 | (2006.01) |
| A01H 5/00 | (2006.01) |

(52) U.S. Cl. ................. 435/469; 800/278; 800/317.2; 800/317.4; 800/284; 800/289; 800/294; 800/298; 800/317.3; 536/23.1; 536/23.2; 536/23.6; 435/320.1; 435/69.1; 435/468; 435/417; 435/410; 435/411; 435/414; 435/419

(58) Field of Classification Search ............ None
See application file for complete search history.

(56) References Cited

U.S. PATENT DOCUMENTS 5,792,920 A * 8/1998 Bridges et al. ............ 800/284

FOREIGN PATENT DOCUMENTS

EP    0 485 044    5/1992
JP    52061286    5/1977

OTHER PUBLICATIONS

Vallelian-Bindschedler et al. Plant Molecular Biology 37(2): 297-308 (May 1998).*
Rodriguez-Lopez et al 2000, Plant biology 97:8705-8710, p. 8710.*
Wang et al 1997, Tha Plant Journal 11:1121-1126, p. 1123.*
Sweetlove et al 1996, Biochemistry Journal 320:493-498, p. 495.*
Iturriaga et al 1992, Plant Molecular Biology 20:555-558, p. 557.*
English Abstract of JP 52061286 dated May 20, 1977.
Vallelian-Bindschedler, L., et al. "Structure, expression and localization of a germin-like protein in barley (*Hordeum vulgare L.*) Tht is insolubilized in stressed leaves." *Plant Molecular Biology*, vol. 37 (1998) pp. 297-308.
Baroja-Fenandez, E., et al. "Distinct isoforms of ADPglucose pyrophosphatase and ADPglucose pyrophosphorylase occur in the suspension-cultured cell of sycamore (*Acer pseudoplatanus L.*)." FEBS Letters, 480 (2000) pp. 277-282.
Rodriguez-Lopez, M., et al. "Adenosine diphosphate glucose pyrophosphatase: A plastidial phosphodiesterase that prevents starch biosynthesis." Proc. Natl. Acad. Sci., 97 (2000) pp. 8705-8710.
Rodriguez-Lopez, M., et al. "Two isoforms of nucleotide-sugar pyrophosphatase/phosphodiesterase from barley leaves (*Hordeum vulgare L.*) are distinct oligomers of HvGLPI, a germin-like protein." FEBS Letters, 490 (2001) pp. 44-48.
Van Dijk, W., et al. "A Universal and Rapid Spectrophotometric Assay of CMP-Sialic Acid Hydrolase and Nucleotide-Diphosphosugar Pyrophosphatase Activities and Detection in Polyacrylamide Gels." Analytical Biochemistry, 117 (1981) pp. 346-353.
Puhakainen, E., et al. "UDPglucuronic Acid Pyrophosphatase Assay with the Aid of Alkaline Phosphatase." Acta Chemica Scandinavica, B 31, No. 2 (1977) pp. 125-129.

* cited by examiner

*Primary Examiner*—David T. Fox
*Assistant Examiner*—Brent T Page
(74) *Attorney, Agent, or Firm*—Ladas & Parry LLP

(57) ABSTRACT

A method for obtaining a transgenic plant that over-expresses a soluble isoform AGPPase enzyme. The method includes a step of transforming a plant with a vector comprising a polynucleotide of SEQ ID NO: 7 linked to a promoter that promotes expression of the polynucleotide in the plant whereby to form the transgenic plant. The transgenic plant has a reduced starch content and a higher resistance to salinity than the plant before the transforming step.

18 Claims, No Drawings

```
                        SEQUENCE LISTING

<160> NUMBER OF SEQ ID NOS: 8

<210> SEQ ID NO 1
<211> LENGTH: 20
<212> TYPE: PRT
<213> ORGANISM: Hordeum vulgare cv. Scarlett
<220> FEATURE:
<223> OTHER INFORMATION: N-terminus of soluble AGPPase

<400> SEQUENCE: 1

Leu Thr Gln Asp Phe Cys Val Ala Asp Leu Thr Cys Ser Asp Thr
                 5                  10                  15

Pro Ala Gly Tyr Pro
                 20

<210> SEQ ID NO 2
<211> LENGTH: 5
<212> TYPE: PRT
<213> ORGANISM: Hordeum vulgare cv. Scarlett
<220> FEATURE:
<223> OTHER INFORMATION: Tryptic sequence of soluble AGPPase

<400> SEQUENCE: 2

Lys Thr Leu Tyr Lys
                 5

<210> SEQ ID NO 3
<211> LENGTH: 8
<212> TYPE: PRT
<213> ORGANISM: Hordeum vulgare cv. Scarlett
<220> FEATURE:
<223> OTHER INFORMATION: Tryptic sequence of soluble AGPPase

<400> SEQUENCE: 3

Lys Ser Val Leu Gly Gly Ser Gly
```

<210> SEQ ID NO 4
<211> LENGTH: 20
<212> TYPE: PRT
<213> ORGANISM: Lycopersicon sculentum
<220> FEATURE:
<223> OTHER INFORMATION: Fragment of the N-terminus obtained by Edman degradation of particulate AGPPase

<400> SEQUENCE: 4

Lys Val Glu Val Cys Glu Ile Asn Leu Lys Leu Leu Tyr Cys Ala
                 5                  10                  15

Asn Gly Ala Lys Phe
             20

<210> SEQ ID NO 5
<211> LENGTH: 30
<212> TYPE: DNA
<213> ORGANISM: Hordeum vulgare cv. Scarlett
<220> FEATURE:
<223> OTHER INFORMATION: Primer of the 5' region of soluble AGPPase

<400> SEQUENCE: 5
gccatggcca acgcaatgtt gctccctgtc                              30

<210> SEQ ID NO 6
<211> LENGTH: 25
<212> TYPE: DNA
<213> ORGANISM: Hordeum vulgare cv. Scarlett
<220> FEATURE:
<223> OTHER INFORMATION: Primer of the 3' region of soluble AGPPase

<400> SEQUENCE: 6
ccgacacgct gacaccacga cgacc                                   25

<210> SEQ ID NO 7
<211> LENGTH: 693
<212> TYPE: DNA
<213> ORGANISM: Hordeum vulgare cv. Scarlett
<220> FEATURE:
<223> OTHER INFORMATION: Soluble cDNA

<400> SEQUENCE: 7
gtagcaagcc atggccaacg caatgttgct ccctgtcctc gtctccttcc tcgtcctgcc      60
cttctccgcc atggccctga cccaggactt ctgcgtcgcc gacctgtcct gcagcgacac     120
gccggcgggg tacccgtgca agaccggcgt cggcgcgggg gacttctact accacggcct     180
cgccgccgcg ggcaacacca gcaacctcat caaggcggcc gtaaccccgg ccttcgtcgg     240
ccagttcccc ggcgtgaacg ggctcggcat ctctgcggcg aggctcgaca tcgccgtggg     300
cggcgtcgtg ccgatgcaca cccacccggc cgcctctgag ctcctcttcg tcactgaggg     360
caccatcttg gcgggcttca tcagctcctc ctccaacacc gtgtacacca agacgctcta     420
caagggcgac atcatggtgt tcccccaggg cctgctccac taccagtaca acggtggcag     480
ctcctccgcg gtagcgctcg ttgcgttcag cggccccaac ccaggcctcc agatcactga     540
ctacgcgctc ttcgccaaca acctgccatc cgccgtcgtt gagaaggtca ccttcttgga     600
cgacgcgcag gtgaagaagc tcaagtccgt gctcggcggc agcggctaat taagcagttc     660
tcagcaaagg tcgtcgtggt gtcagcgtgt cgg                                 693

<210> SEQ ID NO 8

```
<211> LENGTH: 212
<212> TYPE: PRT
<213> ORGANISM: Hordeum vulgare cv. Scarlett
<220> FEATURE:
<223> OTHER INFORMATION: Soluble AGPPase deduced from cDNA

<400> SEQUENCE: 8

Met Ala Asn Ala Met Leu Leu Pro Val Leu Val Ser Phe Leu Val
                  5                  10                  15

Leu Pro Phe Ser Ala Met Ala Leu Thr Gln Asp Phe Cys Val Ala
             20                  25                  30

Asp Leu Ser Cys Ser Asp Thr Pro Ala Gly Tyr Pro Cys Lys Thr
             35                  40                  45

Gly Val Gly Ala Gly Asp Phe Tyr Tyr His Gly Leu Ala Ala Ala
             50                  55                  60

Gly Asn Thr Ser Asn Leu Ile Lys Ala Ala Val Thr Pro Ala Phe
             65                  70                  75

Val Gly Gln Phe Pro Gly Val Asn Gly Leu Gly Ile Ser Ala Ala
             80                  85                  90

Arg Leu Asp Ile Ala Val Gly Gly Val Val Pro Met His Thr His
             95                 100                 105

Pro Ala Ala Ser Glu Leu Leu Phe Val Thr Glu Gly Thr Ile Leu
            110                 115                 120

Ala Gly Phe Ile Ser Ser Ser Ser Asn Thr Val Tyr Thr Lys Thr
            125                 130                 135

Leu Tyr Lys Gly Asp Ile Met Val Phe Pro Gln Gly Leu Leu His
            140                 145                 150

Tyr Gln Tyr Asn Gly Gly Ser Ser Ser Ala Val Ala Leu Val Ala
            155                 160                 165

Phe Ser Gly Pro Asn Pro Gly Leu Gln Ile Thr Asp Tyr Ala Leu
            170                 175                 180

Phe Ala Asn Asn Leu Pro Ser Ala Val Val Glu Lys Val Thr Phe
            185                 190                 195

Leu Asp Asp Ala Gln Val Lys Lys Leu Lys Ser Val Leu Gly Gly
            200                 205                 210

Ser Gly
```

TRANSGENIC PLANTS OVER-EXPRESSING PLANT ADP-GLUCOSE PYROPHOSPHATASE

FIELD OF THE ART TO WHICH THE INVENTION RELATES

The invention relates to the field of production, purification and characterisation of isoforms of the ADPglucose pyrophosphatase (AGPase) enzyme, also called ADPglucose phosphodiesterase, and to the applications of this enzyme in the determination of levels of nucleoside-sugars and sulphonucleotides, and production of transgenic plants in which the AGPase gene is over-expressed, giving rise to plants with reduced starch content and high resistance to salinity.

STATE OF THE PRIOR ART

Starch is the main form of storage of carbohydrates in plants. It is accumulated in large quantities in organs such as seeds (wheat, barley, maize, pea, etc.) and tubercles (potato and sweet potato among others), and it is a fundamental constituent of the human diet. On the other hand, starch is a polymer frequently used in the paper, cosmetics, pharmaceutical and food industries, and is also used as a fundamental component for the manufacture of biodegradable plastics and paints of low environmental impact. Another polysaccharide, cellulose, is a fundamental component of the cell wall of plants, which constitutes the fundamental raw material in industrial processes as important as paper production. As a result, the study of processes implicated in the synthesis of these glucose polymers is a priority topic in different fields of industrial production.

UDPglucose (UDPG) is the fundamental precursor in the biosynthesis of cellulose and polysaccharides of the cell wall. On the other hand, ADPglucose (ADPG) is the universal precursor in the biosynthesis of starch in tissues of plant reserve. Its concentration in the cell determines the quantity and quality of the starch produced by the plant. Reflections on the factors that govern the endogenous levels of ADP in plant cells have centred mainly on their synthesising enzymes, such as ADPG pyrophophorylase (AGPase) and sucrose synthase (Preiss, (1988) "Biosynthesis of starch and its regulation". The Biochemistry of Plants. Vol. 14, Academic Press, New York, pages 182–249; Pozueta-Romero, J., Perata, P., Akazawa, T. (1999) "Sucrose-starch conversion in heterotrophic tissues". Crit. Rev. Plant. Sci. 18, 489–525). However, little research has been carried out on the machinery responsible for the degradation of this nucleotide-sugar (Feingold, D. S., Avigad, G. (1980) "Sugar transformation in plants". The Biochemistry of Plants. Vol. 3. Stumpf, P. K. and Conn, E. E. eds. Academic Press, New York, pages 101–170). There are signs to suggest that both bacteria and mammals have enzymatic machinery capable to hydrolyse nucleotide sugars such as ADPG and UDPG (Melo, A., Glaser, L. (1966) "Nucleotide diphosphate hexose pyrophosphatases". Biochem. Biophys. Res. Commun. 22, 524–531; Bessman, M. J., Frick, D. N., O'Handley, S. F. (1996) "The MutT proteins or Nudix hydrolases, a family of versatile, widely distributed housecleaning enzymes". J. Biol. Chem. 271, 25059–25062; Rodriguez, P., Bass, S. T., Hansen, R. G. (1968) "A pyrophosphatase from mammalian tissues specific for derivates of ADP". Biochim. Biophys. Acta. 167, 199–201; Gasmi, L., Cartwright, J. L., McLennan, A. G. (1999) "Cloning, expression and characterization of YSA1H, a human adenosine 5'-diphosphosugar pyrophosphatase possessing a MutT motif". Biochem. J. 331–337). In plants, such activity has received little attention in the scientific literature (Rodríguez-López, M., Baroja-Fernandez, E., Zandueta-Criado, A., Pozueta-Romero, J. (2000) "Adenosine diphosphate glucose pyrophosphatase: a plastidial phosphodiesterase that prevents starch biosynthesis". Proc. Natl. Acad. Sci., 97, 8705–8710; Baroja-Fernandez, E., Zandueta-Criado, A., Rodríguez-López, M., Akazawa, T., Pozueta-Romera, J. (2000) "Distinct isoforms of ADPglucose pyrophosphatase and ADPglucose" pyrophosphorylase occur in the suspension-cultured cells of sycamore (Acer pseudoplatanus L.). FEBS Lett. 480, 277–282; Rodríguez-López, M., Baroja-Férnandez, E., Zandueta-Criado, A., Moreno-Bruna, B., Muñoz, F. J., Akazawa, T., Pozueta-Romero, J. (2001) "Two isoforms of a nucleotide-sugar pyrophosphatase/phosphodiesterase from barley leaves (Hordeum vulgare L.) are distinct oligomers of HvGLP1, a germin-like protein". FEBS Lett. (in press).

In different industries, starch constitutes an important thickening and setting agent. The biosynthesis of starch in the plant cell from ADPG takes place in the subcellular compartment denominated the plastid. Both the synthesis and the degradation of ADPG are produced in this compartment and, therefore, control of the starch levels may take place through the control of the processes that regulate the ADPG levels. The different applications of starch produced in a plant are based on the balance of amylase and amylopectin, which determines the structure of the starch granule, as well as its viscosity in aqueous suspensions. The proportion of amylase and amylopectin depends on the concentration of ADPG in the plant cell. No process is currently known for regulating the characteristics of starch produced in a plant through control of the degradation of ADPG, which the enzyme described in the present invention may provide.

In addition to acting as a reserve substance for the plant, the starch is accumulated in the plant cell in circumstances in which the plant is not submitted to hydric stress conditions. In conditions in which the plant is submitted to high temperatures or high concentrations of salts in the medium, the plant stops to accumulate starch, producing large quantities of soluble sugars that accumulate in the vacuole (Keeling, P. L., Bacon, P. J., Holt, D. C. (1993) "Elevated temperature reduces starch deposition in wheat endosperm by reducing the activity of soluble starch synthase" Planta 191, 342–348; Geigenberger, P., Geiger, M., Stitt, M. (1998) "High-temperature perturbation of starch synthesis is attributable to inhibition of ADP-glucose pyrophosphorylase by decreased levels of glycerate-3-phosphate in growing potato tubers" Plant Physiol. 117, 1307–1316). In addition to these disorders adapting carbohydrate metabolism to hydric stress, the plant undergoes alterations in its sulphur metabolism, avoiding the accumulation of adenosine-5'-phosphate (PAP) from the transformation of adenosine 5'phosphosulphate (APS) and 3'-phosphoadenosine 5'-phosphosulphate (PAPS) (Gil-Mascarell, R., López-Coronado, J. M., Bellés, J. M., Serrano, R., Rodríguez, P. L. (1999) "The Arabidopsis HAL2-like gene family includes a novel sodium-sensitive phosphatase" Plant J. 17, 373–383). Because of these observations, it is possible that enzymatic reactions responsible for the hydrolysis of ADPG, APS and PAPS are responsible for adaptive processes of the plants to hydric stress conditions.

The chromatographic and radiological techniques constitute a powerful tool in the determination of nucleotide levels such as sulphonucleotides (APS and PAPS among others; Yoshida, H., Fukui, S., Yamashina, I., Tanaka, T., Sakano, T., Usui, T., Shimotsuji, T., Yabuuchi, H., Owada, M., Kitagawa, T. (1982) "Elevation of nucleotide pyrophosphatase activity in skin fibroblasts from patients with Lowe's syndrome". Biochem. Biophys. Res. Commun. 107, 1144–1150) and nucleoside diphosphate sugars (such as derivatives of glucose, ribose, mannose, galactose, glucuronic acid, fructose and galacturonic acid) in crude extracts of animal, plant or microbial origin. Although of a very generalised use, they require high investment in equipment and in the preparation of the test samples. Unfortunately, little use is made of possible alternative methods that allow the detection and quantification of nucleotide sugars and sulphonucleotides in a simple and efficient way. The analysis of the levels in blood, muscle, kidney or liver of some of the aforementioned nucleotide sugars are important in clinical practice (Cortes, P., Dumler, F., Sastry, K. S., Verghese, C. P., Levin, N. W. (1982) "Effects of early diabetes on uridine diphosphosugar synthesis in the rat renal cortex". Kidney Int. 21, 676–682; Spiro, M. J. (1984) "Effect of diabetes on the sugar nucleotides in several tissues of the rat" Diabetologia 26, 70–75; Sochor, M., Kunjara, S., Baquer, N. Z., McLean, P. (1991) "Regulation of glucose metabolism in livers and kidneys of NOD mice". Diabetes 40, 1467–1471). Thus, for example, since UDPglucose is a precursor to glycogen in animals, the analysis of the levels of this molecule may be important in the study and diagnosis of diseases related to carbohydrate metabolism such as for example different types of diabetes. On the other hand, determination of the PAPS levels in urine is fundamental for the diagnosis of severe diseases such as Lowe's syndrome or antiphospholipid syndrome (Yoshida, H., Fukui, S., Yamashina, I., Tanaka, T., Sakano, T., Usui, T., Shimotsuji, T., Yabuuchi, H., Owada, M., Kitagawa, T. (1982) "Elevation of nucleotide pyrophosphatase activity in skin fibroblasts from patients with Lowe's syndrome". Biochem. Biophys. Res. Commun. 107, 1144–1150; Amigo, M. C., Garcia-Torres, T. (2000) "Morphology of vascular, renal, and heart lesions in the antiphospholipid syndrome: relationship to pathogenesis" Curr. Rheumatol. Rep. 2000, 2, 262–270). Obviously, the possibility of analysing the levels of these substances in a sample cheaply and easily constitutes an advantageous alternative with respect to the chromatographic techniques.

The invention describes the purification and applications of an enzymatic product of plant origin that we shall denominate AGPPase that catalyses the hydrolysis of small molecules with phosphodiester or phosphosulphate bonds, of which the most remarkable are ADPG, APS and UDPG as they are the preferred substrates.

The plant enzyme object of the invention presents diverse isoforms in the plant tissues from which it may be obtained (Baroja-Fernández, E., Zandueta-Criado, A., Rodríguez-López, M., Akazawa, T., Pozueta-Romero, J. (2000) "Distinct isoforms of ADPglucose pyrophosphatase and ADPglucose" pyrophosphorylase occur in the suspension-cultured cells of sycamore (*Acer pseudoplatanus* L.), FEBS Lett. 480, 277–282). The isoform that is easiest to extract is that which is denominated soluble, while other isoforms, which we can denominate particulates, are intimately bound to the starch granules, so that it is necessary to destroy the granule by hydrolysing the starch in order to obtain them.

In the present invention it was possible to partially sequence two isoforms of AGPPase; one soluble and another one associated with the granule of starch of the plants. After comparing the fragments sequenced from the soluble isoform with the sequences available in the databanks, it is concluded that it is a protein belonging to the germin-like group whose function was unknown up to date (Vallelian-Bindschedler, L., Mösinger, E., Métraux, J-P., Schweizer, P. (1998) "Structure, expression and localization of a germin-like protein in barley that is insolubilized in stressed leaves". Plant Mol. Biol. 37, 297–308; Hurkman, W. J., Tao H. P., Tanaka, C. K. (1991) "Germin-like polypeptides increase in barley roots during salt stress". Plant Physiol. 97, 366–37; Rodríguez-López, M., Baroja-Fernández, E., Zandueta-Criado, A., Moreno-Bruna, B., Muñoz, F. J., Akazawa, T., Pozueta-Romero, J. (2001) "Two isoforms of a nucleotide-sugar pyrophosphatase/phosphodiesterase from barley leaves (*Hordeun vulgare* L.) are distinct oligomers of HvGLP1, a germin-like protein". FEBS Lett. (in press). The access number of the germin-like protein of barley available in the databank of the EMBL is: Y15962. The extensive distribution of AGPPase in the plant kingdom has been shown after confirming the existence of nucleotide sequences similar to those of the gene of AGPPase of barley in species such as rice (access number AB010876) and *Arabidopsis thaliana* (access number U95034) (Carter, C., Graham, R. A., Thornburg, R. W. (1998) "*Arabidopsis thaliana* contains a large family of germin-like proteins: characterization of cDNA and genomic sequences encoding 12 unique family members" Plant Mol. Biol. 38, 929–943).

The object of the invention is, in a first instance, to obtain a soluble isoform of AGPPase in substantially pure form, from plant tissues, and characterization thereof. Another object of the invention is to obtain the amino acid sequence of soluble barley AGPPase (*Hordeum vulgare*, cv. Scarlett) and its contrast with the sequences available in the databases, identifying the gene that codes it and synthesise a complete cDNA that codes for said protein. Once the gene has been identified, the design of the constructs derived used to obtain transgenic plants with high AGPPase activity will be detailed. The content and quality of starch of these plants, as well as that of the polysaccharides of the cell wall, are modified with respect to the control plants. Such plants do not accumulate the PAP osmotic toxicity marker, and so are more resistant to high salt concentrations than control plants. Another object of the invention is the purification and characterization of an isoform of AGPPase associated to the tomato granule of starch (*Lycopersicon sculentum*), which is also denominated particulate AGPPase.

Another object of the invention is the process followed for the elaboration of devices or kits for determining diphosphate sugar-nucleotides and sulphonucleotides based on the use of the enzymatic product with AGPPase activity. As has been explained in the State of the Prior Art, UDPglucose is the precursor of glycogen in animals, and so its levels in different tissues and organs (blood, muscle, liver) are related to different situations, pathological or not, of the glucose metabolism. For this reason, having kits available for the simple, quick and economical determination of nucleoside sugars would be of great interest for the biomedical products industry, both in the field of diagnostics and for physiological research.

DETAILED DESCRIPTION OF THE INVENTION

Obtaining and purifying the plant product with AGPPase enzymatic activity object of the invention can be carried out from any plant tissue of any species, such as any Monocotyledon or Dicotyledon, such as for example, barley (*Hordeum vulgare*), wheat (*Triticum aestivum*), pepper (*Capsicum annuum*), tomato (*Lycopersicon sculentum*), potato (*Solanum tuberosum*), Arabidopsis (*Arabidopsis thaliana*) or maple (*Acer pseudoplatanus* L.), to mention but a few of the innumerable representative examples from different phyla and genres.

Obtaining and Purifying a Soluble Isoform of AGPPase

The general method for obtaining and purifying soluble plant AGPPase described in the invention includes the following steps, to which small changes can be made without substantially modifying the general scheme of the process of extraction and purification, from any plant tissue:
1. Homogenisation of the plant tissue with an extraction buffer.
2. Filtration through four layers of Miracloth® (filtrating cloth for lactic serum used in cheese industries).
3. Ultracentrifugation of the homogenised filtrate.
4. Precipitation of the proteins from the supernatant in ammonium sulphate.
5. Re-suspension of the precipitate in pH 4.2 buffer.
6. Heating for at least 15 minutes at a temperature between 60 and 65° C.
7. Centrifugation.
8. Concentration of the supernatant and purification of the protein by gel filtration chromatography. The enzymatic activity of the AGPPase is detected by detecting the production of G1P and AMP in samples incubated with ADPG. Optionally, one of the improvements introduced the method described above in the invention consists of the additional use, in the stage of enzyme purification, of a cationic exchange chromatography. Similarly, another of the optional improvements consists of introducing a new stage of chromatography with concanavalin A type affinity columns.
9. Iso-electric focussing. The position of AGPPase can be easily determined in any of the following ways:
    a) Elution of the protein and subsequent detection of the production of G1P in the presence of ADPG.
    b) Incubation of the gel in a solution with bis-paranitrophenylphosphate (bis-PNPP) and development in a basic solution as described by Nishimura and Beevers (Nishimura, M., Beevers, H. (1978) Plant Physiol. 62. 44–48).
10. Separation of the protein by electrophoresis in denaturing gel in a neutral or slightly acidic buffer system such as NuPAGE 4–12% Bis-Tris (Novex, San Diego, Calif.). The position of the AGPPase can be easily determined in one of the following ways:
    a) Elution of the protein and subsequent detection of the production of G1P in the presence of ADPG.
    b) Incubation of the gel in a solution with bis-PNPP and development in a basic solution.

Obtaining and Purifying an Isoform of AGPPase Adhered to the Starch Granule (Particulate Isoform).

The general method for obtaining and purifying particulate plant AGPPase includes the following steps, to which small changes can be made without substantially modifying the general scheme of the process of extraction and purification, from any plant tissue:

1: Homogenisation of the plant tissue with an extraction buffer.
2: Filtration through four stages of Miracloth®.
3: Centrifugation of the homogenised filtrate at 20000 g.
4: Re-suspension of the precipitate in a buffer with 3% Triton X-100.
5: Centrifugation at 20,000 g
6: Re-suspension of the precipitate in a buffer with $MgCl_2$ 200 mM or else with hydrolytic starch enzymes such as α-amylase, β-amylase and amyloglucosidase.
7: Concentration of the supernatant obtained after centrifugation at 20000 g and protein purification by gel filtration chromatography and by ion exchange chromatography. The enzymatic activity of the AGPPase is detected by detecting the production of G1P and AMP in samples incubated with ADPG.
8: Iso-electric focussing. The position of AGPPase can be easily determined in any of the following ways:
    a) Elution of the protein and subsequent detection of the production of G1P in the presence of ADPG.
    b) Incubation of the gel in a solution with bis-paranitrophenylphosphate (bis-PNPP) and development in a basic solution as described by Nishimura and Beevers (Nishimura, M., Beevers, H. (1978) Plant Physiol. 62. 44–48).
9: Separation of the protein by electrophoresis in denaturing gel in a neutral or slightly acidic buffer system such as NuPAGE 4–12% Bis-Tris (Novex, San Diego, Calif.). The position of the AGPPase can be easily determined in one of the following ways:
    a) Elution of the protein and subsequent detection of the production of G1P in the presence of ADPG.
    b) Incubation of the gel in a solution with bis-PNPP and development in a basic solution.

Identification of the Product with AGPPase Enzymatic Activity

The enzymatic product obtained by the processes described above, or other equivalent ones, is identified by the following functional patterns:

It is a pyrophosphatase/phosphodiesterase (EC 3.1.4) that catalyses the hydrolysis of ADPG in equimolar quantities of G1P and AMP (Rodríguez-López, M., Baroja-Fernández, E., Zandueta-Criado, A., Pozueta-Romero, J. (2000) "Adenosine diphosphate glucose pyrophosphatase: a plastidial phosphodiesterase that prevents starch biosynthesis". Proc. Natl. Acad. Sci., 97, 8705–8710).

In addition to ADPG, it recognises small molecules that have phosphodiester and phosphosulphate bonds, such as UDP-glucose, GDP-glucose, GDP-mannose, ADP-mannose, bis-PNPP, PAPS and APS and others of a similar structure.

It does not hydrolyse molecules with phosphomonoester bonds such as G1P, G6P, AMP, 3-phosphoglycerate, and other similar molecules. Nor does it hydrolyse cyclic AMP or long-chain nucleic acids such as DNA or RNA, which are substrates of other phosphodiesterases disclosed in the literature.

Contrary to pyrophosphatases of ADP-sugars (EC 3.6.1.13, EC 3.6.1.21) described in bacteria and animals and contrary to other phosphodiesterases (EC 3.1.4), its ionic requirements are reduced, and so it can work in the absence of ions of magnesium, manganese, cobalt and other divalent cations.

Contrary to pyrophosphatases of sugar-nucleoside diphosphates of bacteria and animals, AGPPase hydrolyses bis-PNPP.

It is inhibited by phosphorylated molecules such as AMP, ADP, ATP, 3-phosphoglycerate, orthophosphate, inorganic pyrophosphate and others of similar characteristics.

It is strongly inhibited by molybdate and arsenate.

It is resistant to ionic detergents such as SDS (sodium dodecylsulphate) (Rodríguez-López, M., Baroja-Fernández, E., Zandueta-Criado, A., Moreno-Bruna, B., Muñoz, F. J., Akazawa, T., Pozueta-Romero, J. (2001) "Two isoforms of a nucleotide-sugar pyrophosphatase/phosphodiesterase from barley leaves (*Hordeun vulgare* L.) are distinct oligomers of HvGLP1, a germin-like protein". FEBS Lett. (in press).

It is resistant to the action of a broad range of proteases, such as K proteinase and pronase (Boehringer).

Its activity is not affected by the action of typical inhibitors of phosphodiesterase such as β-mercaptoethanol, EDTA, reduced cysteine, ascorbate, and other reducing and chelating agents.

It is sensitive to slightly basic pH and is very stable at pH between 4 and 7.5.

Obtaining a Complete cDNA that Codes for Soluble AGPPase

Once the amino acid sequence for AGPPase was known, it was compared with others in the databanks. This allows the gene that codes for AGPPase to be identified. Knowledge of the nucleotide sequence of the gene that codes for AGPPase allowed the creation two specific primers for the AGPPase gene. Making use of these primers, a complete cDNA was amplified by conventional RT-PCR methods and introduced into the EcoRV restriction site of the pSK Bluescript plasmid (Stratagene) giving rise to the AGPPase-cDNApasK construct, which was amplified in the host bacteria *E. Coli* XL1 Blue. Strains of this transformed bacteria were deposited on the Jun. 23, 2000 in the Spanish Collection of Type Cultures (CECT) located in the Edificio de Investigación of the University of Valencia, campus of Burjasot, Burjasot 46100 (Valencia, Spain) with the deposit number CECT 5338.

Obtaining Transgenic Plants that Over-express cDNA of Soluble AGPPase

AGPPase-cDNApsK was sequentially digested with the HindIII, T4 DNA polymerase and XbaI enzymes. The released fragment (which contains cDNA of AGPPase) was cloned in the pVT'BSP plasmid after having been digested sequentially by the NcoI, T4 DNA polymerase and XbaI enzymes. In this way, a plasmid denominated pVT'BSP.GL is obtained, which has a constitutive promoter 35S, cDNA of AGPPase and the Nos terminator.

In order to transfer this construct to the genome of the plants via *Agrobacterium tumefaciens*, it is necessary that it be cloned beforehand in a binary plasmid. To do this, pVT'BSP-GL was sequentially digested with the HindIII, T4 DNA polymerase and XbaI enzymes and cloned within the pCGN1548 binary plasmid (McBride, K. E., Summerfelt, K. R. (1990) "Improved binary vectors for Agrobacterium-mediated plant transformation". Plant Mol. Biol. 14, 269–276) which had been previously digested sequentially with the HindIII, T4 DNA polymerase and XbaI enzymes. The plasmid thus obtained was assigned the name pCGN154835SGL. After amplification in *E. coli* (XL1 Blue), pCGN154835SGL was introduced into *Agrobacterium tumefaciens* (CECT 5387) which was used to transform species such as tomato, tobacco, potato, etc. (Horsch, R. B., Fry, J. E., Hoffmann, N. L., Eichholtz, D., Rogers, S. G., Fraley, R. T. (1985) "A simple and general method for transferring genes into plants" Science 277, 1229–1231. Strains of *Agrobacterium tumefaciens* were deposited at the Spanish Collection of type cultures, located in the Edificio de Investigacón of the University of Valencia, Campus of Burjasot, Burjasot 46100 (Valencia, Spain) with the deposit number CECT5387 on the Jan. 10, 2001.

Elaboration of Assay Devices (Kits) to Determine Sugar-nucleoside Diphosphates and Sulphonucleotides The kits designed for the determination of nucleotides such as sugar-nucleotide diphosphates and sulphonucleotides are based on the action of the product with AGPPase activity on phosphodiester and phosphosulphate bonds of small molecules which, after being hydrolysed, give rise to other molecules that are easy to detect and to quantify.

The two most convenient strategies for the elaboration of these kits start from the hydrolysis of the sugar-nucleoside diphosphate by means of the enzyme object of the present invention, namely, AGPPase, producing equimolar quantities of sugar-1-phosphate and of the corresponding nucleoside mono-phosphate. From here, the determination of the amount of nucleotide initially present in the sample can be undertaken by determining the quantity of sugar-1-phosphate and monophosphate nucleoside produced, as is specified below:

In the case that the sugar-i-phosphate is glucose-i-P (G1P), said compound will be submitted to the action of the phosphoglucomutase enzyme yielding glucose-6-phosphate, which in turn can be made to react by coupling to $NAD^+$ through action of the glucose-6-phosphate dehydrogenase enzyme, to yield 6-phosphogluconate and NADH, which is easily determined.

In the case that the sugar-1-phosphate is not G1P, the determination of the sugar-1-phosphate and the mono-phosphate nucleoside takes place by means of the calorimetric determination of the orthophosphate (Pi) produced after hydrolysis of these compounds with alkaline phosphatase. Alternatively, 5-nucleotidase could be used as coupling enzyme that will hydrolyse the mono-phosphate nucleoside in equimolar quantities of the corresponding nucleoside and Pi. The Pi released in any of the two cases is easily quantifiable by known calorimetric methods.

The strategy for determination of levels of sulphonucleotides such as APS, is based on the hydrolysis of these nucleotides and subsequent production of equimolar quantities of sulphate, which can be determined turbidimetrically or else nephelometrically (Sörbo, B. (1987) "Sulfate: turbidimetric and nephelometric methods" Methods Enzymol. 143, 3–6).

EXAMPLES OF EMBODIMENTS OF THE INVENTION

Some examples are described below in which the process for obtaining and purifying AGPPases in its soluble and particulate isoforms starting from barley leaves is shown in detail. The same process, with minimal variations appropriate for each case, could be applied to any other plant tissue to obtain the corresponding soluble isoforms with the described enzymatic activity. Other examples show the use of AGPPase for the production of kits (assay devices) for determination of sugar-nucleotides and sulphonucleotides.

Another example shows how complete cDNA is obtained which codes for soluble AGPPases. Finally, another example shows how transgenic plants may be obtained.

Example 1

Extraction and Purification of Soluble AGPPase Obtained from Barley Leaves

All the steps were carried out at 4° C., unless otherwise indicated. The plant tissue (200 g) was homogenised with 600 mL of extraction buffer (Mes 50 mM pH 6, EDTA 1 mM, DTT 2 mM) using a Waring blender. The homogenate was filtered through four layers of Miracloth, centrifuged at 100,000 g for 30 minutes and the supernatant was adjusted to 50% of the ammonium sulphate. The precipitate obtained after 30 minutes of centrifugation at 30,000 g (20° C.) was re-suspended in 560 mL of Mes 50 mM pH 4.2, and then heated in a water bath at 62° C. for 20 minutes, cooled on ice, and centrifuged at 30,000 g for 20 minutes. The proteins of the supernatant were precipitated with ammonium sulphate 50% and re-suspended in 5.7 mL of Mes 50 mM pH 6. The sample was then subjected to gel filtration in Superdex 200 column (Pharmacia LKB Biotechnology, Uppsala, Sweden) packed in Mes pH 6 and NaCl 150 mM. It was eluted with the same buffer. The optional improvement consisted of a subsequent purification in a cation exchange column of the Mono S HR 5/5 type (Pharmacia, Uppsala, Sweden) and type Con A Sepharose affinity column (Amersham Pharmacia Biotech, Uppsala, Sweden). The fractions with AGPPase activity were combined and concentrated. The proteins were separated electrophoretically in a NuPage 4–12% Bis Tris gel system (Novex, San Diego, Calif.).

Example 2

Extraction and Purification of Particulate AGPPase Obtained from Tomato Fruit Pericarp All the steps were performed at 4° C., unless otherwise indicated. The plant tissue (30 kg) was homogenised with 30 L of extraction buffer (HEPES 50 mM pH 7, EDTA 1 mM, DTT 2 mM) using a Waring blender. The homogenate was filtered through four layers of Miracloth, centrifuged at 20,000 g for 30 minutes. The precipitate was re-suspended in 1.5 L of extraction buffer with 3% of Triton X-100. The suspension was centrifuged at 20,000 g for 30 minutes, after which the sediment was re-suspended in 0.54 L of extraction buffer with $MgCl_2$ (200 mM) or with α-amylase (100 units/mL), β-amylase (100 units/mL) and amyloglucosidase (15 units/mL). After an hour of stirring, the suspension was centrifuged for half an hour at 20,000 g and the supernatant was dialysed against HEPES 10 mM pH 7 and $MgCl_2$ 10 mM. The dialysed sample was freeze-dried and re-suspended with water to a final volume of 60 mL. The sample was then subjected to gel filtration in Superdex 200 column (Pharmacia LKB Biotechnology, Uppsala, Sweden) packed in HEPES pH 7 and NaCl 150 mM. It was eluted with the same buffer. The fractions that showed AGPPase activity were subjected to a subsequent purification step in a Mono Q type anion exchange column (Pharmacia, Uppsala, Sweden). The fractions with AGPPase activity were combined and concentrated. The proteins were separated electrophoretically in a NuPage 4–12% Bis Tris gel system (Novex, San Diego, Calif.).

Example 3

Enzymatic Assays

Unless indicated to the contrary, all enzymatic reactions were carried out at 37° C. The determinations of the AGPPase activity were carried out using the spectrophotometric determination of G1P in two steps described by Sowokinos (1981) (Sowokinos, 1981, Plant Physiol. 68, 924–929). The reaction mixture contained Hepes 50 mM pH 7, the specified quantity of ADPG and the protein extract in a total volume of 50 microlitres. All assays were carried out against ADPG blanks. After incubating for 20 minutes, the reaction was stopped by boiling in a dry bath for 2 minutes. The mixture was centrifuged at 20,000 g for 5 minutes and the supernatant recovered. In the second step, G1P was determined spectrophotometrically in 300 microlitres of mixture containing Hepes 50 mM pH 7, EDTA 1 mM, $MgCl_2$ 2 mM, KCl 15 mM, $NAD^+$ 0.6 mM, a unit of phosphoglucomutase and another of glucose-6-phosphate dehydrogenase of *Leuconostoc mesenteroides*, and 30 microlitres of supernatant from the first step. After incubating for 20 minutes, NADH production was monitored at 340 nm using a Multiskan EX spectrophotometer (Labsystems). The amount of NADH produced by any protein extract in the absence of ADPG in the first step was negligible.

The native molecular mass of AGPPase was determined by means of gel filtration using a plot of the partition coefficient (Kav) against the logarithm of the molecular mass of the following protein standards: bovine thyroglubulin (670 kDa), bovine gamma-globulin (158 kDa), ovalbumin (45 kDa), myoglobin (17 kDa) and vitamin B-12 (1.3 kDa). The protein content was determined by the Bradford method using the reagent prepared by Bio-Rad and gamma-globulin as a standard.

Tables 1 and 2 presented below show the purification of soluble AGPPase from barley leaves and particulate AGPPase from pericarp of tomato, respectively. The unit (U) is defined as the amount of enzyme that catalyses the production of 1 μmol of product per minute.

TABLE 1

| | Total volume (mL) | Total protein (mg) | Total activity (mU) | Specific activity (mU/mg protein) | Purification (factor) | Yield (%) |
|---|---|---|---|---|---|---|
| Crude extract | 560 | 5107.8 | 105000 | 20.6 | — | 100 |
| Supernatant 100000 × g | 520 | 3436.7 | 100500 | 29.2 | 1.4 | 95.7 |
| Ammonium sulphate 50% | 520 | 748.6 | 97500 | 130.2 | 6.3 | 92.8 |
| pH 4.2/ 62° C. | 520 | 24.9 | 90500 | 3634 | 176.4 | 85.2 |
| Ammonium sulphate 50% | 5.7 | 8.1 | 47300 | 5839 | 283.4 | 45.0 |
| Superdex 200 | 1.7 | 1.3 | 30200 | 23230 | 1127.6 | 28.7 |
| NuPAGE SDS Electrophoresis | 1.7 | 0.026 | 30000 | 1161500 | 56350 | 28 |

TABLE 2

|  | Total volume (L) | Total protein (mg) | Total activity (mU) | Specific activity (mu/mg protein) | Purification (factor) | Yield (%) |
|---|---|---|---|---|---|---|
| Crude extract | 45 | 6000 | 51000 | 2.8 | 1 | 100 |
| Sediment 20000 × g | 1.5 | 1860 | 36000 | 19.3 | 6.9 | 70 |
| Triton sedimentation | 0.54 | 1680 | 36000 | 21.4 | 7.6 | 70 |
| MgCl$_2$ supernatant | 0.54 | 750 | 30000 | 40 | 14.2 | 58 |
| Superdex 200 | 0.13 | 36 | 8100 | 225 | 80.3 | 16 |
| Mono-Q | 0.057 | 1.5 | 100 | 66 | 23.6 | 0.2 |

Example 4

Identification of the Product Obtained with Enzymatic Activity

The product with AGPPase activity thus obtained complies with the following characteristics:
  Both the soluble and particulate AGPPase are phosphodiesterases that catalyse the hydrolysis of ADPG producing equimolar quantities of G1P and AMP.
  In addition to ADPG, both isoenzymes recognise other small molecules that have phosphodiester bonds, such as UDP-glucose, GDP-glucose, bis-PNPP and others of similar structure. They also catalyse the hydrolysis of small molecules with phosphosulphate bonds, such as PAPS and APS, releasing equimolar quantities of sulphate and the corresponding nucleotide.
  They do not hydrolyse molecules with phosphomonoester bonds such as G1P, G6P, AMP, 3-phosphoglycerate, and other similar bonds. Nor do they hydrolyse cyclic AMP or nucleic acids such as DNA and RNA, which are substrates of other phosphodiesterases described in the literature.
  Their ion requirements are small, so that they can work in the absence of magnesium, manganese, cobalt ions and other divalent cations, which are fundamental effectors for other phosphodiesterases disclosed in the literature.
  Contrary to pyrophosphatases of nucleoside diphosphate sugars of bacteria and animals, both isoforms hydrolyse bis-PNPP.
  They are inhibited by phosphorylated molecules such as AMP, ADP, ATP, 3-phosphoglycerate, orthophosphate, inorganic pyrophosphate and others of similar characteristics.
  They are strongly inhibited by molybdate and arsenate.
  They are resistant to the ionic detergents such as SDS (sodium dodecylsulphate).
  They are resistant to the action of a broad range of proteases, such as K proteinase and pronase (Boehringer).
  Their activity is not affected by the action of typical inhibitors of phosphodiesterase such as β-mercaptoethanol, EDTA, reduced cysteine, ascorbate, and other reducing and chelating agents.
  They are sensitive to slightly basic pH and they are very stable at a pH between 4 and 7.5. This is one of the features that makes both isoforms of AGPPase into enzymes completely different from most phosphodiesterases described in the literature, as the latter enzymes are stable and active at slightly basic pHs.
  Michaelis-Menten constant ($K_m$) for ADP-glucose, of 0.5 mMolar, which is four of five times lower than the $K_m$ corresponding to other nucleotide sugar substrates such as ADP-ribose, UDP-glucose or similar combinations. The APS affinity is similar to the affinity for ADP-glucose.

Some of the particular characteristics of soluble AGPPase are:
  Soluble AGPPase is resistant at a temperature of 65° C. for 30 minutes, and can be characterised by the following data:
  Apparent molecular weight measured by gel filtration around 35–55 kDa.
  Reaction $K_{qq'}$ of 110
  Increase in Standard Free Energy (ΔG') of −2.9 kCal/mol.
  In the present invention, the characterisation of the amino acid sequence allows us to know another series of characteristics such as:
  It is a glycoprotein
  Apparent molecular weight of the protein purified on natured gels around 20 kDa.
  The sequences of amino acids obtained by means of Edman degradation are:
    N-terminus: SEQ ID NO.: 1
    Internal sequences (obtained after partial hydrolysis of the AGPPase with trypsin): SEQ ID NO.: 2 and 3

Some of the particular characteristics of particulate AGPPase are:
  Molecular weight as measured by gel filtration around 400–500 kDa.
  Apparent molecular weight in peptide denaturing gel that comprises the particulate AGPPase: 45 kDa.
  The amino acid sequence obtained by means of Edman degradation is:
    N-terminus: SEQ ID NO.: 4

Example 5

Obtaining a Complete cDNA that Codes for Soluble AGPPase

Knowledge of the nucleotide sequence of the gene that codes for the priming AGPPase allows the creation of two specific primers of the AGPPase gene whose sequences are, in 5'-3' sense, SEQ ID NO.: 5 and SEQ ID NO.: 6. Using these primers, a complete cDNA was amplified by RT-PCR conventional methods. This was then introduced into the pSK Bluescript plasmid (Stratagene) and amplified in the XL1 Blue host bacteria. The molecular weight of the peptide deduced from the cDNA is 19.5 kDa. The cDNA sequence is SEQ ID NO.: 7.

Example 6

Products from Different Plants with AGPPase Activity

The AGPPase enzyme is widely distributed among plants, such that the enzymatic product with AGPPase activity can be obtained from any plant. By way of example, the following Table II is presented with the specific activities (mU/mg protein) obtained in various Monocotyledons and Dicotyledons.

TABLE 3

| | Specific activity (mU/mg protein) (+ADPG) |
|---|---|
| Monocotyledons | |
| Barley leaf (Hordeum vulgare) | 113.7 ± 3.5 |
| Wheat leaf (Triticum aestivum) | 22.4 ± 2.5 |
| Dicotyledons | |
| Arabidopsis thaliana (Wt) leaf | 5.2 ± 0.6 |
| Pepper leaf (Capsicum annuum) | 5.0 ± 0.6 |
| Tomato leaf | 5.6 ± 0.6 |
| (Lycopersicon sculentum) | 5.6 ± 0.6 |
| Cell culture of maple | 16.5 ± 7.2 |
| (Acer pseudoplatanus) | |

Example 7

Elaboration of Enzymatic Kits for Determining Nucleoside Diphosphate Glucose

For the determination of nucleoside diphosphate glucose such as ADPG, UDP-glucose, CDP-glucose, GDP-glucose and TMP-glucose, a kit was elaborated containing the following elements:
 a. AGPPase
 b. NAD
 c. Phosphoglucomutase (PGM)
 d. G6P dehydrogenase (G6PDH)
 e. Buffer The determination of the quantity of nucleoside diphosphate glucose present in the test sample was based on spectrophotometric determination of the NADH produced according to the following coupled reaction:

(Test sample)
NDP-glucose $\xrightarrow{\text{AGPPase}}$ NMP + G1P $\xrightarrow{\text{PGM}}$ G6P $\xrightarrow[\text{NADH}]{NAD^+ \quad G6PDH}$ 6-phosphogluconate The determination of the quantity of NDP-glucose in a test sample would take place by the elaboration of a cocktail whose composition would be (for 1 ml):
 Test sample
 1 U of AGPPase
 1 U of PGM
 1 U of G6PDH
 0.6 mM NAD
 Mes or Hepes buffer 50 mM pH 7
 Water (making volume up to 1 ml)

The mixture is incubated at 37° C. for 20 minutes and the variation in absorbance of the sample at 340 nm is observed. As a negative control, a cocktail may be used in which the AGPPase is missing.

Example 8

Elaboration of Enzymatic Kits for Determination of Nucleoside Diphosphate Sugars other than Glucose The determination kits are prepared for the following nucleoside diphosphate sugars:
 Nucleoside diphosphate ribose (ADP-ribose, GDP-ribose, UDP-ribose, CDP-ribose or TDP-ribose)
 Nucleoside diphosphate mannose (ADP-mannose, GDP-mannose, TDP-mannose, UDP-mannose or CDP-mannose)
 Nucleoside diphosphate galactose (ADP-galactose, GDP-galactose, UDP-galactose or CDP-galactose)
 Nucleoside diphosphate glucouronate (GDP-glucuronate, UDP-glucuronate, ADP-glucuronate, CDP-glucuronate or TDP-glucuronate)
 Nucleoside diphosphate fructose (GDP-fructose, ADP-fructose, CDP-fructose, UDP-fructose or TDP-fructose)
 Nucleoside diphosphate galacto-uronate (UDP-galacto-uronate, GDP-galacto-uronate, CDP-galacto-uronate, TDP-galacto-uronate or ADP-galacto-uronate)

The following elements are included in the kit:
 a. AGPPase
 b. 5'-nucleotidase (or, alternatively, alkaline phosphatase)
 c. buffer The determination of the quantity of nucleoside diphosphate sugar present in the test sample is based on the calorimetric determination of the orthophosphate released according to the following coupled enzyme reaction:

(test sample)
NDP-sugar $\xrightarrow{\text{AGPPase}}$ sugar-P + NMP $\xrightarrow{\text{5'-nucleotidase}}$ base + Pi The determination of Pi takes place according to any of the many calorimetric methods available in the literature and on the market.

The determination of the amount of NDP-sugar in a test sample will be performed by the elaboration of a cocktail (1 ml) composed of:
 Test sample
 1 U of AGPPase
 1 U of 5'-nucleotidase (or, alternatively, 1 U of alkaline phosphatase)
 Mes or Hepes buffer 50 mM pH 7.5
 Water (making volume up to 1 ml)

The mixture is incubated at 37° C. for 20 minutes and the production of Pi released determined according to conventional techniques. As a negative control, a cocktail may be used in which AGPPase is missing.

Example 9

Elaboration of an Enzymatic Kit for the Determination of PAPS and APS

The strategy for determining the levels of sulphonucleotides such as PAPS or APS is based on the turbidimetric determination or nephelometric determination according to the following reaction:

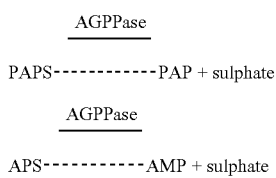

Determination of the quantity of sulphonucleotide in a test sample would take place by means of the elaboration of a cocktail (1 ml) composed of:

Test sample

1 U AGPPase

Mes or Hepes buffer 50 mM pH 7.0

Water (making volume up to 1 ml)

The mixture is incubated at 37° C. for 20 minutes and the production of sulphate released is determined by conventional techniques. As a negative control, a cocktail may be used in which the AGPPase is missing.

Example 10

Obtaining Transgenic Plants of Tobacco, Potato and Tomato that Over-express AGPPase Using the strain of *Agrobacterium tumefaciens* CECT 5387 tobacco plants were obtained (*Nicotiana tabacum*), potato (*Solanum tuberosum*) and tomato (*Lycopersicon sculentum*) with high AGPPase activity in all organs analysed (root, leaf, fruit and stem). These plants presented the following characteristics:

1. Low starch and carbohydrate content of the cell walls (according to the measuring techniques based on commercial kits described in the literature (Frehner, M., Pozueta-Romero, J., Akazawa, T. (1990) "Enzyme sets of glycolysis, gluconeogenesis and oxidative pentose phosphate pathway are not complete in nongreen highly purified amyloplasts of sycamore cell suspension cultures" Plant Physiol. 94, 538–544)).
2. High soluble sugar content such as sucrose, glucose-6-phosphate, glucose and fructose.
3. Reduction in levels of PAP accumulated in tissues, conferring great resistance to high concentrations of sodium chloride in the growth substrate with respect to non-transformed plants.
4. The external morphology of the plant was not aberrant, after being compared with that of untransformed plants.

The invention claimed is:

1. A method for obtaining a transgenic plant comprising transforming a plant with a vector that causes the plant to over-express a soluble isoform AGPPase enzyme, said vector comprising the polynucleotide of SEQ ID NO:7 operably linked to a promoter that promotes expression of the polynucleotide in the plant.

2. The method according to claim 1, wherein the transgenic plant has a reduced starch content and a higher resistance to salinity than the plant before the transforming.

3. The method according to claim 1, wherein the plant is transformed with a strain of Agrobacterium tumefaciens comprising said polynucleotide.

4. The method according to claim 3, wherein the strain is Agrobacterium tumefaciens strain CECT 5387.

5. The method according to claim 1, wherein the plant is a dicotyledonous plant.

6. The method according to claim 5, wherein the plant is tomato.

7. The method according to claim 5, wherein the plant is tobacco.

8. The method according to claim 5, wherein the plant is potato.

9. The method according to claim 1, wherein the promoter is a constitutive CaMV35S promoter.

10. The transgenic plant obtained by the method of claim 1.

11. The transgenic plant obtained by the method of claim 2.

12. The transgenic plant obtained by the method of claim 3.

13. The transgenic plant obtained by the method of claim 4.

14. The transgenic plant obtained by the method of claim 5.

15. The transgenic plant obtained by the method of claim 6.

16. The transgenic plant obtained by the method of claim 7.

17. The transgenic plant obtained by the method of claim 8.

18. The transgenic plant obtained by the method of claim 9.

* * * * *